US00PP36803P2

(12) United States Plant Patent
Kerley et al.

(10) Patent No.: US PP36,803 P2
(45) Date of Patent: Jul. 1, 2025

(54) PRIMULA PLANT NAMED 'KERBELBLUWAT'

(50) Latin Name: *Primula vulgaris*
Varietal Denomination: KERBELBLUWAT

(71) Applicant: Kerley & Co, Willingham (GB)

(72) Inventors: David William Kerley, Over (GB); Timothy Edward Kerley, Willingham (GB)

(73) Assignee: Kerley & Co. Ltd. (GB)

( * ) Notice: Subject to any disclaimer, the term of this patent is extended or adjusted under 35 U.S.C. 154(b) by 0 days.

(21) Appl. No.: 18/799,748

(22) Filed: Aug. 9, 2024

(51) Int. Cl.
*A01H 5/02* (2018.01)
*A01H 6/00* (2018.01)

(52) U.S. Cl.
USPC ..... Plt./472

(58) Field of Classification Search
USPC ..... Plt./472
CPC ..... A01H 5/02; A01H 5/00; A01H 6/00
See application file for complete search history.

(56) References Cited

PUBLICATIONS

Kerley & Co Primula Belarina Baltic Blue, retrieved on Nov. 8, 2024 at https://www.kerley.co.uk/variety/baltic-blue/, 2 pp. (Year: 2024).*

* cited by examiner

*Primary Examiner* — June Hwu
(74) *Attorney, Agent, or Firm* — Cassandra Bright

(57) ABSTRACT

A new and distinct cultivar of *Primula* plant named 'KERBELBLUWAT' is described, characterized by abundant, fully-double blue flowers, and dark green foliage. Plants have compact, uniform habits. The new variety is a *Primula*, normally used as an ornamental garden or landscape plant.

2 Drawing Sheets

Latin name of the genus and species: *Primula vulgaris*.
Variety denomination: 'KERBELBLUWAT'.

BACKGROUND OF THE INVENTION

The new cultivar is the product of a planned breeding program under the direction of the inventors. *Primula* 'KERBELBLUWAT' resulted from the crossing of the seed parent, an unpatented, unnamed, proprietary variety of *Primula*, and the pollen parent, a different unnamed, unpatented, proprietary variety of *Primula*. The crossing resulting in the new variety was made in April of 2017 at a research greenhouse in Cambridge, United Kingdom. Selection of the new variety 'KERBELBLUWAT' was made in March of 2018, by the inventors at a research greenhouse located in Cambridge, United Kingdom.

Asexual reproduction of the new cultivar 'KERBELBLUWAT' was first performed in Cambridge, the United Kingdom during May of 2018, by tissue culture. This and subsequent propagation has shown that the unique features of this cultivar are stable and reproduced true to type in successive generations.

SUMMARY OF THE INVENTION

The cultivar 'KERBELBLUWAT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERBELBLUWAT'. These characteristics in combination distinguish 'KERBELBLUWAT' as a new and distinct *Primula* cultivar:

1. Double flowers.
2. Mid-blue flower color.
3. Abundant flowering.
4. Compact and uniform plant habit.
5. Dark green leaf color.

PARENT COMPARISONS

Plants of the new cultivar 'KERBELBLUWAT' are similar to plants of the seed parent, in most horticultural characteristics. However, plants of the new cultivar differ in the following ways:

1. Flowers of the new variety are double, while flowers of the seed parent are single.
2. Flowers of the new variety are sterile, while flowers of the seed parent are fertile.

Plants of the new cultivar 'KERBELBLUWAT' are similar to plants of the pollen parent, in most horticultural characteristics. However, plants of the new cultivar differ in the following ways:

1. Flowers of the new variety are double, while flowers of the pollen parent are single.
2. Flowers of the new variety are sterile, while flowers of the pollen parent are fertile.

COMMERCIAL COMPARISON

Plants of the new variety can be compared to plants of the proprietary *Primula* cultivar 'Kerbelbubid', unpatented.

Plants of the new *Primula* differed from plants of the cultivar 'Kerbelbubid' in the following characteristics:

1. Flowers of the new variety are smaller than flowers of this comparator.
2. The calyx of the new variety is shorter than the calyx of this comparator.
3. Flower color of the new variety is a darker blue than the flower color of this comparator.

BRIEF DESCRIPTION OF THE PHOTOGRAPHS

Figure 1:
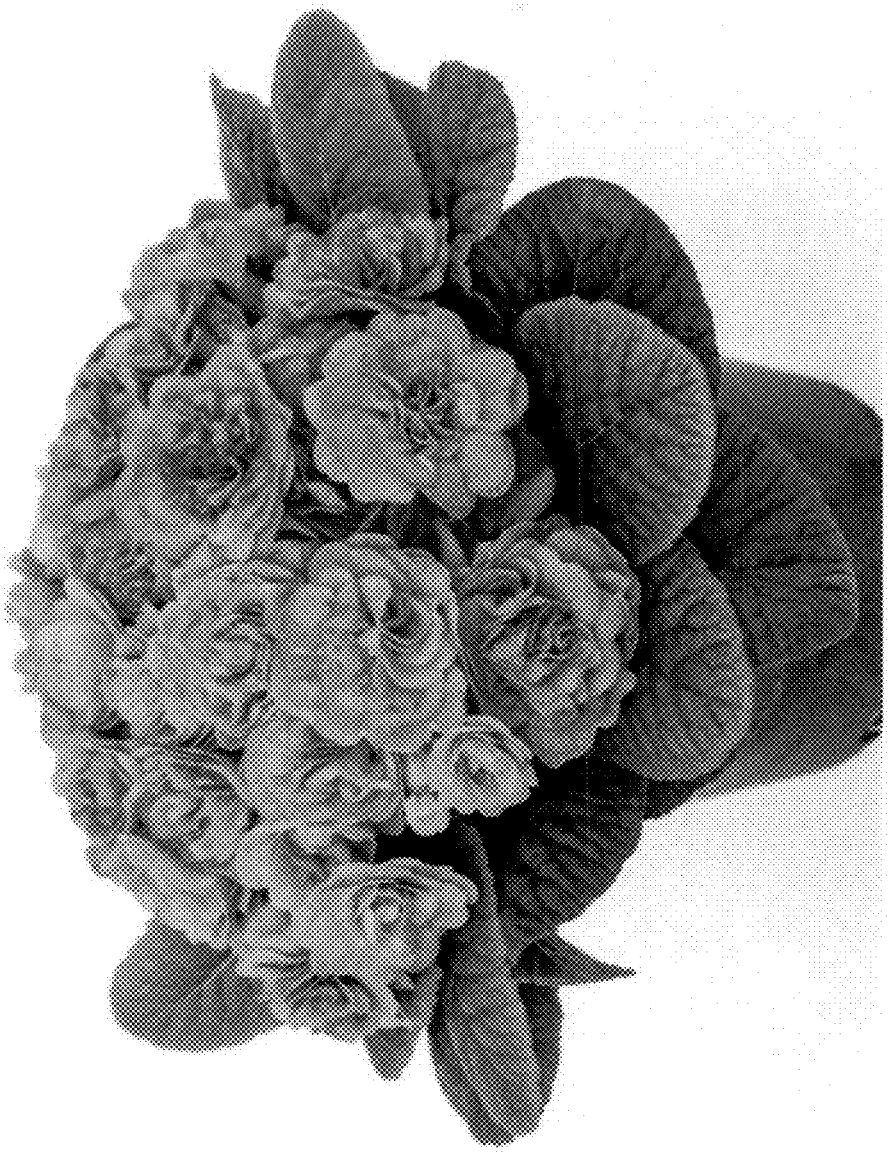

The accompanying photograph in FIG. 1 illustrates in full color a typical plant of 'KERBELBLUWAT' grown in Over, Cambridge, United Kingdom, in a glass-covered greenhouse. This plant was about 7 months old when the photographs were taken. During the production of the plants, day temperatures ranged from 5° to 15° C. and night temperatures ranged from 2° to 12° C.

Figure 2:
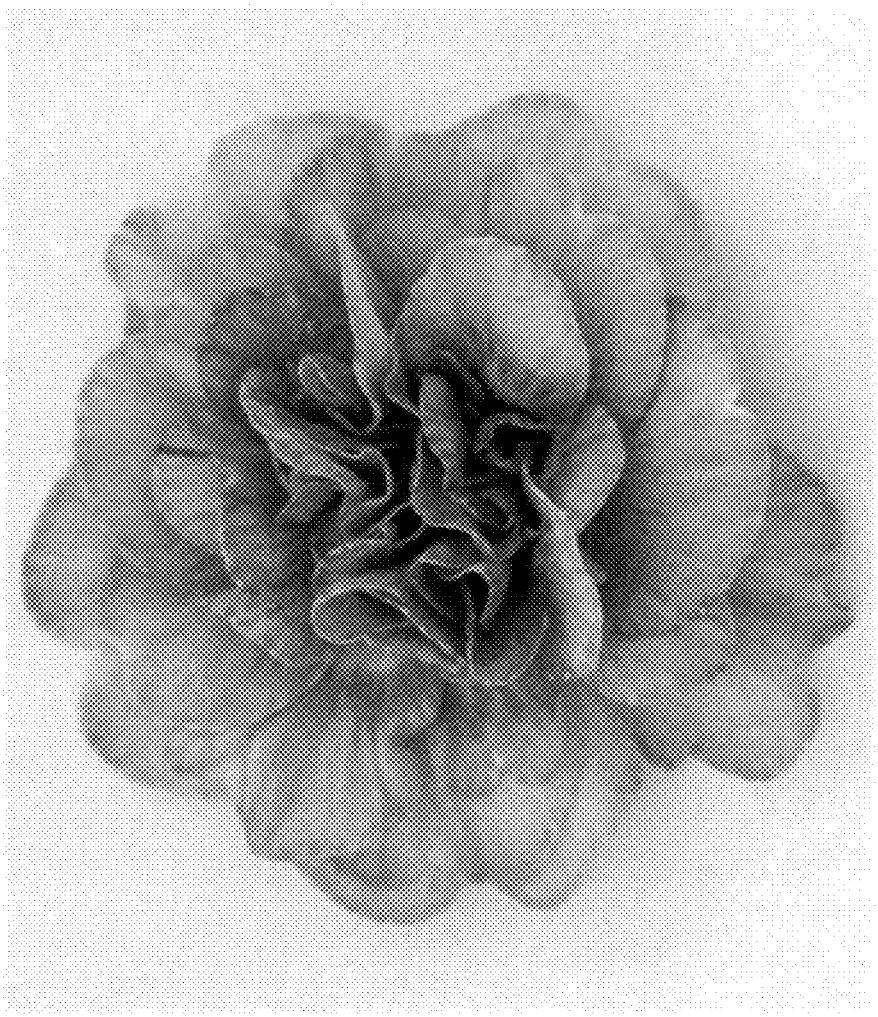

FIG. 2 illustrates a close-up view of a typical flower of 'KERBELBLUWAT'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 except where general terms of ordinary dictionary significance are used. The following observations and measurements describe 'KERBELBLUWAT' plants grown in a greenhouse in Cambridge, United Kingdom. During the production of the plants, day temperatures ranged from 1.5° C. to 25° C. and night temperatures ranged from 1.5° C. to 15° C. No chemical or photoperiodic treatments were given. Measurements were taken during Spring and numerical values represent averages of typical flowering types.

Botanical classification: *Primula vulgaris* 'KERBELBLUWAT'.

PROPAGATION

Method: Tissue culture.

Time to produce a rooted plant: About 6 weeks at 20° C.

Root description: Fibrous, colored RHS White 155A.

PLANT

Plant form/habit: Upright, compact and uniform; mounded.

Height: 12 cm.

Plant spread: 25 cm.

Branching characteristics: No branches, foliage emerges basally.

Vigor: Vigorous.

FOLIAGE

Leaf:

*Arrangement*.—Basal, simple.

*Length*.—9 cm.

*Width*.—4.1 cm.

*Shape*.—Oblanceolate.

*Apex*.—Obtuse, rounded.

*Base*.—Acute.

*Margin*.—Slightly crenate, irregular, undulating.

*Texture of top surface*.—Slightly rugose.

*Texture of bottom surface*.—Rugose with prominent venation.

*Color*.—Developing foliage upper side: RHS Yellow-Green 146B. Developing foliage under side: RHS Yellow-Green 144A. Mature foliage upper side: RHS Yellow-Green 146A. Mature foliage under side: RHS Yellow-Green 146B.

*Venation*.—Type: Pinnate. Venation color upper side: RHS Yellow-Green 193A. Venation color under side: RHS Yellow-Green 193A.

Petiole:

*Length*.—1.2 cm.

*Diameter*.—0.3 cm.

*Color*.—Upper Surface: RHS Yellow-Green 195C. Lower Surface: RHS Yellow-Green 195D.

*Texture upper surfaces*.—Glabrous.

*Texture lower surfaces*.—Slightly pubescent.

FLOWER

Bloom period: Recurrent flowering during the Spring under United Kingdom outdoor conditions.

Flower type/habit: Solitary, rounded double flowers facing upright and outward. Each flower framed by enlarged calyx.

Persistence: Persistent.

Fragrance: None.

Flowers per inflorescence: 60 to 80 flowers and buds per plant.

Flower bud:

*Height*.—1.4 cm.

*Diameter*.—0.6 cm.

*Shape*.—Conical.

*Color*.—RHS Yellow-Green 144D.

*Texture*.—Glabrous.

Individual flower:

*Diameter*.—4.7 cm.

*Depth*.—2.6 cm.

*Corolla tube average length*.—1 cm.

Petals:

*Quantity*.—25 to 35 per flower, in several concentric whorls.

*Length* (*including tube*).—2.6 cm.

*Width*.—1.7 cm.

*Shape*.—Obcordate.

*Apex*.—Emarginate.

*Margin*.—Entire, slightly undulating.

*Texture, upper and lower surfaces*.—Glabrous.

*Longevity*.—8 to 9 days.

*Color*.—Developing petals, upper surface: Eye of RHS Yellow 17A, with a slight surround of White 155B, changing to Purple-Blue 97C, with a hint of Purple-Blue 97B at the margin. Developing petals, lower surface: Hint of RHS Yellow 2B at base, changing to White 155C, then Purple-Blue 97C and 97D, getting darker towards the margin. Mature petals, upper surface: Eye of RHS Yellow 17A, with a slight surround of White 155B, changing to a tonal blend of Purple-Blue 97A, B, and C. Often 97A present at margin. Inner petals show more 97A which gives a tonal affect to the flower. Subtle venation color of Violet-Blue 92A. Mature petals, lower surface: RHS Yellow 8D at base, with White 155D changing to Purple-Blue 97C, with irregular marks of 97A and 97B.

Flower throat:
*Diameter.*—0.4 cm.
*Texture.*—Glabrous.
*Color.*—RHS Yellow 160B.

Flower tube:
*Diameter.*—0.3 cm.
*Texture.*—Glabrous.
*Color.*—RHS Yellow 160D.

Calyx:
*Depth.*—1 cm.
*Diameter.*—1.5 cm.

Sepals:
*Quantity.*—5 in a single whorl; fused at base.
*Length.*—1.5 cm.
*Width.*—0.5 cm.
*Shape.*—Oblanceolate.
*Apex.*—Acute.
*Margin.*—Entire.
*Texture upper surface.*—Glabrous.
*Texture lower surface.*—Glabrous with prominent lower vein.
*Color, upper surface.*—RHS Yellow-Green 146D.
*Color, lower surface.*—RHS Yellow-Green 146C.

Botanical bract: Not present.

Peduncle:
*Length.*—9.2 cm.
*Diameter.*—0.2 cm.
*Orientation.*—Upwards and outwards.
*Strength.*—Medium.
*Color.*—RHS Yellow-Gray 156A, with slight blush of Purple-Red 186C.
*Texture.*—Slightly pubescent.

REPRODUCTIVE ORGANS

Development of reproductive organs has not been observed.

OTHER CHARACTERISTICS

Disease resistance: Plants of the new *Primula* have not been noted to be resistant nor susceptible to pathogens and pests common to *Primula.*

Temperature tolerance: Plants of the new *Primula* have been observed to have tolerated temperatures from about −5° to 28° C.

Fruit/seed production: Fruit and seed production not observed; flowers are sterile.

What is claimed is:

1. A new and distinct cultivar of *Primula* plant named 'KERBELBLUWAT' as herein illustrated and described.

* * * * *